United States Patent [19]
Roberts

[11] Patent Number: 5,155,863
[45] Date of Patent: Oct. 20, 1992

[54] REMOVABLE PROTECTIVE COVER FOR BREATHING MASK

[76] Inventor: Johniece T. Roberts, 3567 65th Ave. Cir. East, Sarasota, Fla. 34243

[21] Appl. No.: 704,818

[22] Filed: May 23, 1991

[51] Int. Cl.$^5$ .......................... A61F 9/00; A62B 7/00; A62B 25/00
[52] U.S. Cl. .......................................... 2/15; 2/432; 2/9; 128/202.13; 128/206.12; 128/206.21
[58] Field of Search .................. 2/15, 10, 12, 9, 173, 2/433, 434, 432, 46, 5, 206, 424; 128/202.13, 206.12, 206.17, 206.21, 380, 858

[56] References Cited

U.S. PATENT DOCUMENTS

| | | | |
|---|---|---|---|
| 3,629,870 | 12/1971 | Paisley | 2/15 |
| 4,038,979 | 8/1977 | McCosker | 2/9 |
| 4,579,113 | 4/1986 | McCreadie et al. | 128/202.13 |
| 4,790,031 | 12/1988 | Duerer | 2/15 |
| 4,908,878 | 3/1990 | Tarragano | 2/15 |
| 5,040,530 | 8/1991 | Bauer et al. | 128/206.12 |

FOREIGN PATENT DOCUMENTS

| | | | |
|---|---|---|---|
| 1022302 | 3/1966 | United Kingdom | 2/9 |
| 2211098 | 6/1989 | United Kingdom | 128/206.12 |

Primary Examiner—Werner H. Schroeder
Assistant Examiner—Michael A. Neas
Attorney, Agent, or Firm—Charles J. Prescott

[57] ABSTRACT

A removable protective cover and blackout for a lens of a face and breathing mask. The device includes a flexible fabric sheet similar in size and shape to that of a transparent viewing lens of the mask and having an elastic band sewn to the perimeter of the sheet forming a gathered elastic hem sized to fit around the lens frame of the mask. When so positioned, the main central portion of the fabric sheet is against or immediately adjacent the outer surface of the viewing lens. The fabric material for the sheet may be either totally or partially light occlusive and may also include a central aperture in alignment with a connector in the viewing lens for connection to an air intake modulator.

5 Claims, 1 Drawing Sheet

REMOVABLE PROTECTIVE COVER FOR BREATHING MASK

BACKGROUND OF THE INVENTION

This invention is related generally to protective face and breathing masks, and more particularly to a protective cover and blackout for the viewing lens for such masks.

One of the essential pieces of equipment utilized in fire rescue is a self-contained breathing apparatus (S.C.B.A.). These devices are in the form of a face mask for shielding the user's face and for introducing air or oxygen into the cavity of the mask when sealed against the user's face. The air is distributed through a modulator from a separate hose-connected storage tank which the user carries by hand or by body strap.

During training exercises, it is desirable to simulate fire rescue conditions. One of those conditions experienced during fire rescue is a partial or total lack of visibility due to smoke from a fire. To simulate this condition during training, a plastic trash bag is placed over the user's head or tape or cling gauze is applied over the viewing lens so as to totally block out light to the user's eyes. However, the plastic trash bag unrealistically interferes with other training exercises and the adhesive or tape or cling gauze is difficult to remove from the transparent lens of the face mask.

An additional problem occurs with these masks in that they are routinely mishandled and tossed about when not in use into various compartments of the fire fighting equipment. This results in a rapid scratching and abrasive deterioration of the transparent lens which is typically a high-impact resistant plastic material. When these lenses become sufficiently scratched so as to diminish effective viewability therethrough, the mask must be discarded.

The following prior art devices are known for providing light occlusive devices as follows:
Paisley, U.S. Pat. No. 3,629,870
Duerer, U.S. Pat. No. 4,790,031
Tarragano, U.S. Pat. No. 4,908,878

The present invention provides for a removable protective cover and blackout which will serve to facilitate practice exercises and also to prevent scratching of the transparent lens with the mask when not in use.

BRIEF SUMMARY OF THE INVENTION

This invention is directed to a removable protective cover and blackout for a lens of a face and breathing mask. The device includes a flexible fabric sheet similar in size and shape to that of a transparent viewing lens of the mask and having an elastic band sewn to the perimeter of the sheet forming a gathered elastic hem sized to fit around the lens frame of the mask. When so positioned, the main central portion of the fabric sheet is against or immediately adjacent the outer surface of the viewing lens. The fabric material for the sheet may be either totally or partially light occlusive and may also include a central aperture in alignment with a connector in the viewing lens for connection to an air intake modulator.

It is therefore an object of this invention to provide a removable blackout cover for fire fighting face and breathing masks which, when installed over the viewing lens of the mask, will either partially or totally blacken the view of the user during fire rescue training.

It is another object of this invention to provide a removable blackout cover for fire fighting face and breathing masks which is economical to manufacture and which will not interfere with other fire fighting activities.

It is yet another object of this invention to provide a removable protective cover for preventing scratches and abrasions of the transparent lens of a fire rescue breathing mask when not in use.

In accordance with these and other objects which will become apparent hereinafter, the instant invention will now be described with reference to the accompanying drawings.

DETAILED DESCRIPTION OF THE INVENTION

Figure 1:
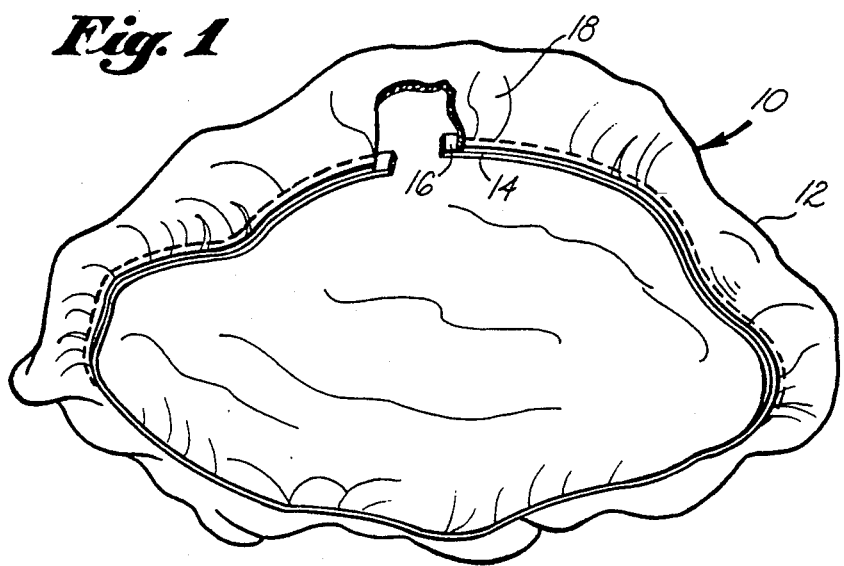
FIG. 1 is a perspective partially broken view of the preferred embodiment of the invention.
Figure 2:
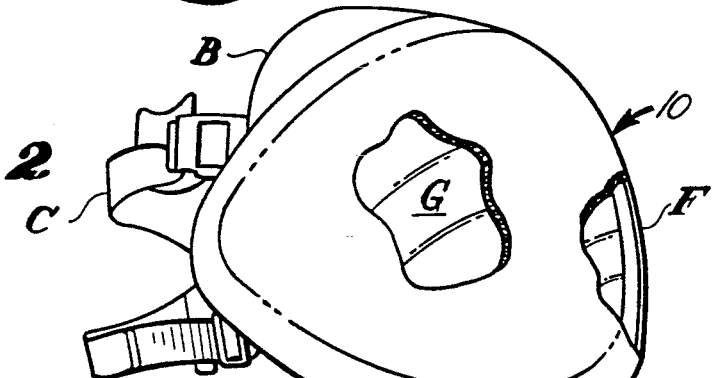
FIG. 2 is a perspective partially broken view of the invention as shown in FIG. 1 installed around the frame of the transparent viewing lens.

Referring now to the drawings, and particularly to FIGS. 1 and 2, the preferred embodiment of the invention is shown generally at numeral 10. This device 10 includes a flexible fabric sheet 12 having a length of elastic 16 sewn to the perimeter of sheet 12 so as to form a hem 14. The elastic band 16 in its free configuration is shorter than the length of the perimeter of sheet 12 in-the-flat so as to gather the material at 18 adjacent hem 14.

The overall shape of sheet 12 is such that the hem 14 is generally configured to stretchably fit around the frame F of a fire rescue breathing mask A. These masks A include an air intake modulator M which is interengaged to the lower portion of flexible housing B as shown. An air hose H is connected at one end to modulator M and at the other end to a source of air or oxygen which the user either carries or has strapped to his body (not shown).

The mask A is structured such that flexible housing B fits generally around the user's eyes, nose and mouth, and is held thusly by head straps C. A transparent viewing lens G fitted securely within frame F thus forms a chamber in combination with housing B and the user's face, into which air or oxygen is fed by modulator M.

By this arrangement, when the device 10 is in place as shown in FIG. 2 elastically around frame F, the entire transparent viewing lens G is covered. The flexible material sheet 12 thus serves to both protect the outer surface of lens G and to be light occlusive with respect to the user. The preferred material for fabricating sheet 12 is a 65% polyester/35% cotton blend having a black color so as to be totally light occlusive.

Figure 3:
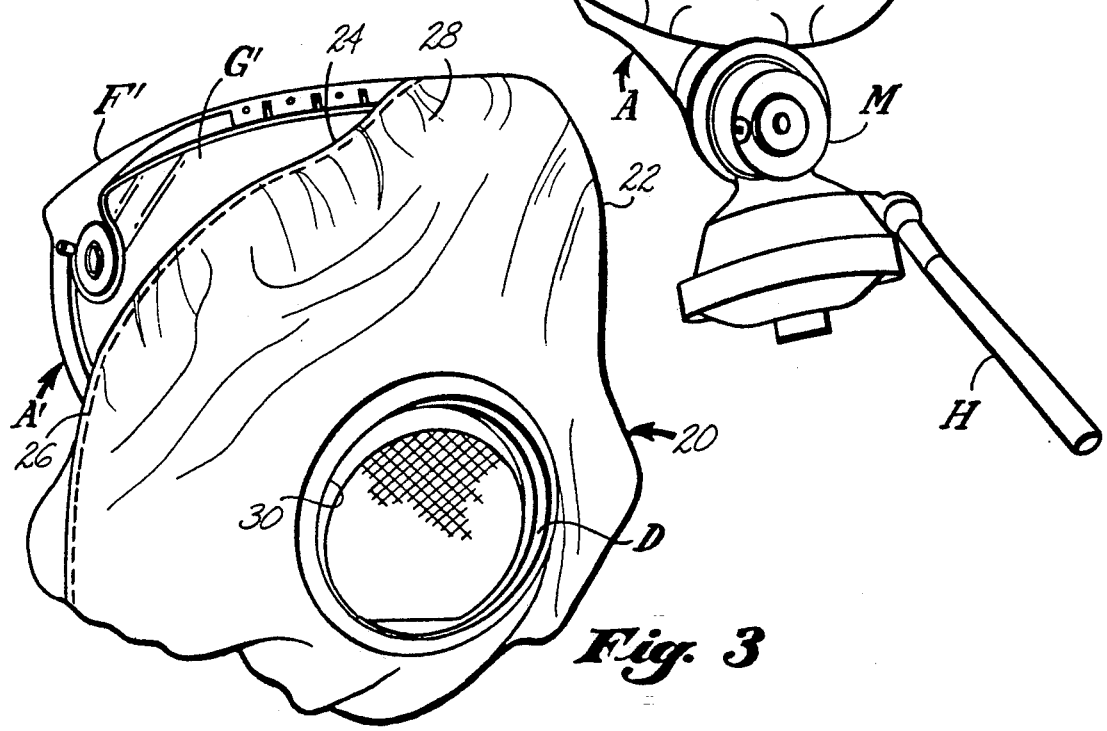
FIG. 3 is a perspective view of another embodiment of the invention shown partially installed over another form of a fire rescue breathing mask.

Referring now to FIG. 3, an alternate embodiment of the invention is shown generally at numeral 20. This embodiment 20 is fabricated of a flexible material sheet 22 having an elastic band 26 around the perimeter of sheet 22 to form hem 24 as previously described. Gathering pleats 28 thus result because the elastic band 26 is shorter than the overall perimeter of cover 22 in-the-flat.

This embodiment 20 is structured to accommodate a fire rescue breathing mask A' which includes a frame F' securely housing a transparent viewing lens G' Lens G' includes a ring connector D which is structured to receive a removable modulator (not shown). Thus, this embodiment 20 includes an hemmed aperture 30 formed into a central portion of cover 22 which is in alignment and register with connector D so as to allow for the releasable installation of the modulator (not shown) when the device 20 is in place around frame F'.

The fabric utilized in sheet 22 in this embodiment 20 is of a similar blend of polyester and cotton as previously described. However, the thread density is such that the material is only partially light occlusive. This modification still provides the desired protection against scratches and abrasions to the exposed surface of lens G'. However, a predetermined degree of light will be transmitted to the user so as to simulate a lesser degree of smoke density during a training session rather than to totally blind the user during practice sessions.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A removable protective cover and blackout for a viewing lens of a face and breathing mask comprising:
    a flexible fabric sheet having an overall shape similar in size and shape to that of a transparent protective viewing lens of the face mask;
    said sheet having a gathered elastic perimeter structured to elastically fit around a lens frame of the face mask so as to position a main central portion of said sheet directly against the outer surface of the viewing lens.

2. A removable protective cover and blackout for a face and breathing mask as set forth in claim 1, wherein:
    said sheet is formed of a fabric which is totally light occlusive.

3. A removable protective cover and blackout for a face and breathing mask as set forth in claim 2, wherein:
    said sheet includes a hemmed central aperture sized and positioned to align with a connector in the viewing lens for connection to an air intake modulator.

4. A removable protective cover and partial blackout for a viewing lens of a face and breathing mask comprising:
    a flexible fabric sheet which is partially light-transmissive having an overall shape similar in size and shape to that of a transparent protective viewing lens of the face mask;
    said sheet having a gathered elastic perimeter structured to elastically fit around a lens frame of the face mask so as to position a main central portion of said sheet directly against the outer surface of the viewing lens.

5. A removable protective cover and partial blackout for a face and breathing mask as set forth in claim 4, wherein:
    said sheet includes a hemmed central aperture sized and positioned to align with a connector in the viewing lens for connection to an air intake modulator.

* * * * *